(12) United States Patent
Gondalia et al.

(10) Patent No.: US 12,191,019 B2
(45) Date of Patent: Jan. 7, 2025

(54) SYSTEMS AND METHODS FOR IMPROVING RESPIRATORY MEDICAMENT DEVICE USAGE

(71) Applicant: Reciprocal Labs Corporation, Madison, WI (US)

(72) Inventors: Rahul Bhailal Gondalia, San Francisco, CA (US); Leanne Kaye, Redwood City, CA (US); David Stempel, Clyde Hill, WA (US); Robert Baddeley, Madison, WI (US); Amber Michelle Markey, Madison, WI (US); Meredith A. Barrett, Redwood City, CA (US); Melissa Williams, Sellersburg, IN (US)

(73) Assignee: RECIPROCAL LABS CORPORATION, Madison, WI (US)

( * ) Notice: Subject to any disclaimer, the term of this patent is extended or adjusted under 35 U.S.C. 154(b) by 0 days.

(21) Appl. No.: 17/429,612

(22) PCT Filed: Feb. 13, 2020

(86) PCT No.: PCT/US2020/018198
§ 371 (c)(1),
(2) Date: Aug. 9, 2021

(87) PCT Pub. No.: WO2020/168138
PCT Pub. Date: Aug. 20, 2020

(65) Prior Publication Data
US 2022/0115107 A1    Apr. 14, 2022

Related U.S. Application Data

(60) Provisional application No. 62/805,934, filed on Feb. 14, 2019.

(51) Int. Cl.
*G16H 20/30* (2018.01)
*G16H 20/13* (2018.01)
(Continued)

(52) U.S. Cl.
CPC ............. *G16H 20/30* (2018.01); *G16H 20/13* (2018.01); *G16H 40/63* (2018.01); *G16H 80/00* (2018.01)

(58) Field of Classification Search
CPC ........ G16H 20/30; G16H 40/63; G16H 20/13; G16H 80/00
See application file for complete search history.

(56) References Cited

U.S. PATENT DOCUMENTS 9,550,031 B2 *  1/2017  Van Sickle ........... A61M 15/00
10,019,555 B2    7/2018  Manice et al.
(Continued)

FOREIGN PATENT DOCUMENTS

CN    106999681 A  *  8/2017  ............. A61B 5/087
CN    108135534 A  *  6/2018  ........... A61B 5/7275
(Continued)

OTHER PUBLICATIONS

Anderson, W.C. et al., "Screening for inhalation technique errors with electronic medication monitors," The Journal of Allergy and Clinical Immunology: In Practice 7(6), Jul. 2019, pp. 2065-2067.
(Continued)

*Primary Examiner* — Kenneth Bartley
(74) *Attorney, Agent, or Firm* — McDermott Will & Emery LLP

(57) ABSTRACT

Systems and methods to determine and ensure proper usage technique of a respiratory medicament device for a respiratory ailment. Medication data relating to a medication plan for a patient is collected and used to determine the respiratory medicament device type in use. For respiratory medi-
(Continued)

cament device types requiring multiple consecutive uses, use data is collected and used to determine proper or improper use technique based on the timing between consecutive uses of the respiratory medicament device. Notifications of proper or improper usage technique are provided based on the determined usage technique. Real-time monitoring of the use data is used to provide directions on the required timing of consecutive uses of the respiratory medicament device and thus ensure proper usage technique.

20 Claims, 6 Drawing Sheets

(51) Int. Cl.
  G16H 40/63 (2018.01)
  G16H 80/00 (2018.01)

(56) References Cited

U.S. PATENT DOCUMENTS

| | | | | |
|---|---|---|---|---|
| 10,957,447 | B2* | 3/2021 | Hogg | G16H 40/63 |
| 2002/0065685 | A1* | 5/2002 | Sasaki | G16H 10/65 |
| | | | | 705/3 |
| 2009/0194104 | A1* | 8/2009 | Van Sickle | G16H 40/63 |
| | | | | 128/203.12 |
| 2015/0100335 | A1* | 4/2015 | Englehard | G16H 40/63 |
| | | | | 705/2 |
| 2015/0174349 | A1* | 6/2015 | Tunnell | A61M 15/009 |
| | | | | 128/200.14 |
| 2016/0256639 | A1* | 9/2016 | Van Sickle | G16H 20/13 |
| 2017/0072144 | A1* | 3/2017 | Van Sickle | A61M 15/008 |
| 2017/0109493 | A1* | 4/2017 | Hogg | G16H 10/60 |
| 2017/0140125 | A1* | 5/2017 | Hogg | A61M 15/009 |
| 2021/0082582 | A1* | 3/2021 | Barrett | A61M 15/00 |
| 2021/0161213 | A1* | 6/2021 | Woodbine | G16H 40/67 |
| 2021/0361888 | A1* | 11/2021 | Pocreva, III | A61K 38/28 |
| 2022/0115107 | A1* | 4/2022 | Gondalia | G16H 10/20 |

FOREIGN PATENT DOCUMENTS

| | | | | |
|---|---|---|---|---|
| CN | 105492057 B | * | 5/2019 | A61M 15/0026 |
| EP | 3375473 A1 | * | 9/2018 | A61M 11/00 |
| GB | 2556016 A | * | 5/2018 | A61M 15/00 |
| JP | H-07509378 A | | 9/2000 | |
| JP | 2017-535396 A | | 11/2017 | |
| JP | 2018-520803 A | | 1/2021 | |
| JP | 2022521722 A | * | 4/2022 | |
| WO | WO-2011089490 A1 | * | 7/2011 | A61M 15/0065 |
| WO | WO-2014004437 A1 | * | 1/2014 | A61M 15/0005 |
| WO | WO 2015/178907 A1 | | 11/2015 | |
| WO | WO-2016172614 A1 | * | 10/2016 | G06N 20/00 |
| WO | WO-2018167278 A1 | * | 9/2018 | A61M 11/00 |
| WO | WO-2019209994 A1 | * | 10/2019 | A61B 5/087 |
| WO | WO-2020168138 A1 | * | 8/2020 | A61M 15/008 |

OTHER PUBLICATIONS

Global Initiative for Asthma, "Global Strategy for Asthma Management and Prevention," 2016 Update, Available from: www.ginasthma.org, pp. 1-151.
Levy, M.L. et al., "Asthma patients; inability to use a pressurised metered-dose inhaler (pMDI) correctly correlates with poor asthma control as defined by the Global Initiative for Asthma (GINA) strategy: a retrospective analysis," Primary Care Respiratory Medicine 22(4), Dec. 2013, pp. 406-411.
Lewis, A. et al., "The economic burden of asthma and chronic obstructive pulmonary disease and the impact of poor inhalation technique with commonly prescribed dry powder inhalers in three European countries," BMC Health Services Research, vol. 16, Jul. 12, 2016, pp. 1-12.
National Heart, Lung, and Blood Institute, "National Asthma Education and Prevention Program: Expert Panel Report 3: Guidelines for the Diagnosis and Management of Asthma," Full report 2007, Aug. 28, 2007, pp. 1-440.
Nurmagambetov, T. et al., "The Economic Burden of Asthma in the United States, 2008-2013" Annals of the American Thoracic Society, vol. 15, No. 3, Mar. 2018, pp. 348-356.
Plaza, V. et al., "Errors in the Use of Inhalers by Health Care Professionals: A Systematic Review," The Journal of Allergy and Clinical Immunology: In Practice, vol. 6, Iss. 3, May 2018, pp. 987-995.
Price, D. et al., "Inhaler competence in asthma: Common errors, barriers to use and recommended solutions," Respiratory Medicine, vol. 107, Oct. 23, 2012, pp. 37-46.
Price, D.B. et al., "Inhaler Errors in the CRITIKAL Study: Type, Frequency, and Association with Asthma Outcomes," Journal of Allergy and Clinical Immunology: In Practice, vol. 5, Iss. 4, Mar. 9, 2017, pp. 1071-1081.e9.
Sanchis J. et al., "Systematic Review of Errors in Inhaler Use: Has Patient Technique Improved Over Time?" Chest, vol. 150, Iss. 2, Aug. 2016, pp. 394-406.
Shim C. et al., "The adequacy of inhalation of aerosol from canister nebulizers," The American Journal of Medicine, vol. 69, Iss. 6, Dec. 1980 pp. 891-894.
Szefler, S.J. et al., "Quantifying beta agonist utilization: occasions or puffs?," The Journal of Allergy and Clinical Immunology: In Practice, vol. 7, Iss. 3, Mar. 2019, pp. 1088-1090.
Usmani, O.S. et al., "Critical inhaler errors in asthma and COPD: a systematic review of impact on health outcomes," Respiratory Research, vol. 19, Article 10, Jan. 16, 2018, pp. 1-20.
Wheaton, A.G. et al., "Employment and activity limitations among adults with chronic obstructive pulmonary disease—United States, 2013," MMWR Morbidity and Mortality Weekly Report 64(11), Mar. 27, 2015, pp. 289-295.
PCT International Search Report and Written Opinion, International Application No. PCT/US2020/018198, dated May 12, 2020, 20 Pages.
Kuha, J., "AIC and BIC: Comparisons of Assumptions and Performance," Sociological Methods & Research, vol. 33, No. 2, Nov. 2004, pp. 188-229.
JIPO—Examination Report mailed Jan. 9, 2024 for Japanese Appln. No. 2021-547876, English and Japanese translations, 6 pages.

* cited by examiner

SYSTEMS AND METHODS FOR IMPROVING RESPIRATORY MEDICAMENT DEVICE USAGE

TECHNICAL FIELD

The present disclosure relates generally to systems and methods of improving treatment for patients with respiratory ailments. More specifically, it concerns identifying technique errors based on the timing of consecutive medicament doses with electronic medication monitors, and subsequent digital interventions with patients in order to enhance proper medicament device usage.

BACKGROUND

Respiratory ailments, such as asthma and chronic obstructive pulmonary disease (COPD), remain a significant and costly public health problem. For example, in the United States, more than 25 million people have asthma. Worldwide, the World Health Organization estimates the population with asthma may be 235 million, and predicts that it will rise by 2025. Similarly, recent studies by the Centers for Disease Control and Prevention have listed COPD as the third leading cause of death in the United States while estimating more than 15 million people may have COPD induced impaired lung function (Wheaton, A. G., Cunningham, T. J., Ford, E. S., Croft, J. B., Employment and activity limitations among adults with chronic obstructive pulmonary disease—United States, b 2013. *MMWR Morb. Mortal Wkly. Rep.*, 2015, 64(11), 290-295).

Despite the development of new medications, rates of hospitalizations and emergency room visits have not declined. Each year in the United States asthma causes approximately 2 million emergency department visits, 500,000 hospitalizations, and 5,000 deaths. In addition, asthma is responsible for an estimated 5.2 million missed days of school, and 8.7 million days of work (Nurmagambetov, T., Kuwahara, R., Garbe, P., The Economic Burden of Asthma in the United States, 2008-2013., *Ann. Am. Thorac. Soc.*, 2018, 15(3), 348-356). Total annual costs are almost US$82 billion (ibid). COPD causes approximately 715,000 hospitalizations, and 134,000 deaths annually. Additionally, the cost to the nation for COPD was recently projected to be approximately US$49.9 billion, including US$29.5 billion in direct health care expenditures, US$8.0 billion in indirect morbidity costs and US$12.4 billion in indirect mortality costs.

Many asthma exacerbations could be prevented with currently available treatments, however, only 1 in 5 asthmatics has the disease under control. Such treatments often rely on identifying a triggering condition of an asthma condition and properly administering treatment such as a medicament. One mechanism for a patient to self-administer a medicament is an inhaler. When a trigger event occurs, a patient may administer the medicament via a puff from the inhaler.

Similarly, persons with COPD often carry an inhaled medication to immediately relieve symptoms whenever or wherever they occur. The frequency and location with which patients use these medications are important indicators of how well the disease is controlled and treated. The Centers for Disease Control and Prevention has recommended that temporal and geographic specificity of COPD surveillance data be monitored to improve COPD treatment. Currently, healthcare providers are limited to a retrospective analysis of small proportions of attacks that led to emergency room visits and hospitalizations (i.e., the most severe exacerbations). These in-patient visits may indicate where the patient lives or the location of the health facility where they received treatment, but provide no precise information about when or where their exacerbation began.

Revised national guidelines urge doctors to more closely monitor whether prescribed treatment for either asthma or COPD is controlling everyday symptoms and improving quality of life. Healthcare providers, however, are limited by an availability of tools to assess how well their patients are doing on a day-to-day basis. An increasing number of physicians have begun to use periodic, written questionnaires (e.g., the COPD Assessment Test (CAT)) to monitor patients and determine their level of control. These instruments require patients to accurately recall and report the frequency of symptoms, medicament device (e.g. inhaler) usage, and activity level and restriction over some period of time, usually two to four weeks. As a result, collected information relating to management of respiratory disorders has been subject to error introduced by biases (e.g. fallible recollection), different interpretations of symptoms, and behaviors (e.g. non-adherence), and extremely limited frequency of data collection such that the data is of limited utility.

Although study results vary, estimates of inhaler errors include up to 90% of patients using pressurized metered dose inhalers (pMDIs) and up to 54% of patients using dry powder inhalers (DPIs). Inadequate inhaler technique lowers drug deposition to the lungs, wastes medication and may lead to poor disease control, reduced quality of life, increased exacerbations leading to emergency hospital admissions and higher treatment costs (Usmani, O. S., Lavorini, F., Marshall, J. et al. Critical inhaler errors in asthma and COPD: a systematic review of impact on health outcomes. *Respir. Res.* 19, 10, 2018). There is increasing evidence to suggest that correct inhaler technique plays an important role in improving medicine adherence, clinical outcomes, quality of life and use of healthcare utilization.

The therapeutic efficacy of inhaled medications in asthma and COPD is commonly hindered by errors in inhalation technique. To achieve full therapeutic efficacy of an inhaled asthma medication, several specific steps are required as discussed in asthma guidelines and the patient information leaflets (PILs) for these medications. Guidelines state that training is required with follow-up observation of inhalation technique. A recent meta-analysis described deficient knowledge by health care providers (HCPs) of the appropriate steps required for maximum deposition of these medications in the airways (Plaza, V., Giner, J., Rodrigo, G. J., Dolovich, M. B., Sanchis, J., Errors in the Use of Inhalers by Health Care Professionals: A Systematic Review. *J. Allergy Clin. Immunol. Pract.*, 2018; 6, 987-95). Criteria to evaluate inhalation technique are subjective and therefore assessment can be challenging.

Following the required steps needed for maximal therapeutic benefit has been discussed for decades. Shim and Williams decades ago reported the difficulty of training and knowledge retention of inhalation technique in patients (Shim, C., Williams, Jr. M. H., The adequacy of inhalation of aerosol from canister nebulizers, *Am. J. Med.*, 1980; 69, 891-4). This issue was described as inhaled corticosteroids were introduced into asthma pharmacotherapy in the 1980*s*. While most providers agree inhalation technique is important, they may not be taking an active role to regularly assess inhalation technique. As such, improvements in inhalation technique have not been observed (Sanchis, J., Gich, I., Pedersen, S., Systematic Review of Errors in Inhaler Use: Has Patient Technique Improved Over Time? Chest., 2016, 150, 394-406).

For many rescue and controller medications, two administrations are required for a dose. Both US and global asthma guidelines have explicit recommendations regarding patient education training, observation and retraining for metered dose inhalers (MDIs) (National Heart Lung and Blood Institute, National Asthma Education and Prevention Program, Expert panel report 3: guidelines for the diagnosis and management of asthma, Full report 2007; Global Initiative for Asthma, Global Strategy for Asthma Management and Prevention, 2019, available from www.ginasthma.org). Additionally, PILs provide instructions on appropriate use that is consistent across medication types and brands. Over 30-60 seconds are required between administrations to achieve effective metered dose inhaler use including shaking the canister, exhaling completely before inhalation, inhaling slowly, and breath-holding after inhalation.

As such, there is a need for a system that allows for objective characterization of medication usage techniques. There is a further need for a system that allows collection of data based on medication use (such as asthma controller and rescue medicament use) to identify individual patients, and particular groups of patients, employing improper medication usage techniques. There is a further need for a system that identifies improper medication use and provides notifications to the patient, clinical provider and/or caregiver to highlight improper use and how such use can and should be improved.

SUMMARY

The present inventors have discovered that objective assessment of the interval between two administrations of medication is a useful measure to screen for inadequate technique. This was achieved by identifying medication use error(s) by quantifying the time between two consecutive administrations using electronic medication monitors (EMMs), i.e. medicament device sensors. Thus, the present invention provides for the identification of medication use timing technique issues with dynamic interventions for multiple users in multiple modalities.

Accordingly, in a first aspect of the invention, there is provided a system to determine usage technique of a respiratory medicament device for a respiratory ailment, the system comprising: a communication interface to collect medication data relating to a medication plan for a patient and to collect use data of a respiratory medicament device for delivering controller or rescue respiratory medicament to the patient; a storage device to store the collected medication data and to store the collected use data; and a data analysis module operable to: based on the collected medication data, identify whether the medicament device type requires a plurality of consecutive uses of the respiratory medicament device; based on the collected use data, determine the timing between consecutive uses of the respiratory medicament device; based on the timing of consecutive uses of the respiratory medicament device, classify the consecutive uses as proper or improper usage technique to generate a usage technique record; and provide at least one notification of proper or improper usage technique based on the usage technique record to ensure proper usage technique. Advantageously, this system facilitates the analysis of respiratory medicament device usage events for devices requiring consecutive use, and is particularly suited to the remote analysis of medicament usage events transmitted to the system via the communication interface from medicament devices monitored by medicament sensors.

The collected medication data may include information regarding at least one of a medicament type, a medicament device type, and a prescribed number of doses. For example, the collected medication data may include information on the period of time required between consecutive doses of a plurality of medicament types or medicament device types.

The plurality of consecutive uses is usually two consecutive uses of the respiratory medicament device, with the two uses being separated in time by less than or equal to 120 seconds.

In this instance, proper usage technique may comprise a time period of greater than 30 seconds between consecutive uses of the respiratory medicament device, whereas improper usage technique may comprise less than or equal to 30 seconds between consecutive uses of the respiratory medicament device.

The at least one notification of proper or improper usage technique can be provided electronically to at least one of the patient, a caregiver and a health provider. Such notifications may identify improper usage technique and provide guidance on an appropriate usage technique for the respiratory medicament device. Guidance can comprise a timer configured to indicate the period of time required between consecutive uses of the respiratory medicament device, or may comprise audio and/or visual content displaying the required sequence of steps for ensuring proper usage technique of the respiratory medicament device. The notifications can be provided, after classifying the consecutive uses as proper or improper, on an immediate basis or delayed according to a predetermined time schedule.

Additionally, the system may further comprise a client device, which is a portable computing device, the client device being in communication with the storage device and the communication interface. The portable computing device can include an application such that the at least one notification of proper or improper usage technique is provided by way of the application.

In this embodiment, the use data may be detected by a medicament sensor which is in association with the respiratory medicament device, such as wherein the medicament sensor is detachable from or integrated with the respiratory medicament device.

In accordance with the first aspect of the invention, there is also provided a method of determining usage technique of a respiratory medicament device for a respiratory ailment, the method comprising: collecting medication data relating to a medication plan for a patient; collecting use data of a respiratory medicament device for delivering controller or rescue respiratory medicament to the patient; transmitting the medication data and the use data to a storage device; storing the medication data and the use data in the storage device; based on the collected medication data, identifying whether the medicament device type requires a plurality of consecutive uses of the respiratory medicament device; based on the collected use data, determining the timing between consecutive uses of the respiratory medicament device; based on the timing of consecutive uses of the respiratory medicament device, classifying the consecutive uses as proper or improper usage technique to generate a usage technique record; and providing at least one notification of proper or improper usage technique based on the usage technique record to ensure proper usage technique.

In a second aspect of the invention, there is provided a system to ensure proper usage technique of a respiratory medicament device for a respiratory ailment, the system comprising: a communication interface to collect medication data relating to a medication plan for a patient and to collect use data of a respiratory medicament device for delivering controller or rescue respiratory medicament to the patient; a storage device to store the collected medication data and to store the collected use data; and an instruction component to provide guidance in response to collected use data indicating a use of the respiratory medicament device; and a data analysis module operable to: based on the collected medication data, determine whether the medicament device in use requires a plurality of consecutive uses; based on the collected use data, identify a first detected use of the respiratory medicament device; based on the first detected use of the respiratory medicament device, provide guidance by way of the instruction component to direct a second use of the respiratory medicament device according to a predetermined time schedule. Beneficially, the system is able to provide guidance and coaching to users in order to ensure that consecutive doses of medication are taken on the correct timescale. It is particularly suited to embodiments in which a client device, such as a portable computing device, provides the guidance to take the second dose of medication via an associated application on the client device, wherein the communication interface receives notification of the first use event from a sensor associated with a medicament device in real time.

The collected medication data may include information regarding at least one of a medicament type in use, a medicament device type in use, and a prescribed number of doses. For example, the collected medication data may include information on the period of time required between consecutive doses of a plurality of medicament types or medicament device types.

The predetermined time schedule can direct the second use of the respiratory medicament device after greater than 30 seconds following the first detected use.

The use data may be detected by a medicament sensor associated with the medicament device, such as wherein the medicament sensor is configured to be attachable to or is integrated with the respiratory medicament device.

The system may form part of a client device, which is a portable computing device, and the instruction component may form part of an application on the portable computing device.

In certain embodiments, the instruction component is capable of providing audio and/or visual commands to direct the second use of the respiratory medicament device, such as wherein the audio and/or visual commands comprise a timer set to the predetermined time schedule. The audio and/or visual guidance may comprise direction on the required sequence of steps to ensure proper usage technique of the respiratory medicament device.

In accordance with the second aspect of the invention, there is also provided a method of ensuring proper usage technique of a respiratory medicament device for a respiratory ailment, the system comprising: collecting medication data relating to a medication plan for a patient; collecting use data of a respiratory medicament device for delivering controller or rescue respiratory medicament to the patient; transmitting the medication data and the use data to a storage device; storing the medication data and the use data in the storage device; based on the collected medication data, determining whether the medicament device in use requires a plurality of consecutive uses; based on the collected use data, identifying a first detected use of the respiratory medicament device; and based on the first detected use of the respiratory medicament device, providing guidance by way of an instruction component to direct a second use of the respiratory medicament device according to a predetermined time schedule.

In a third aspect of the invention, there is provided a medicament sensor to ensure proper usage technique of a respiratory medicament device for a respiratory ailment, the medicament sensor comprising: at least one sensor to detect use of a respiratory medicament device for delivering controller or rescue respiratory medicament to a patient; a storage device to store medication data relating to the patient's medication plan and to store use data relating to the detected use of the respiratory medicament device; an instruction component to provide guidance in response to the detected use of the respiratory medicament device; and a data analysis module operable to: based on the medication data, determine whether the medicament device in use requires a plurality of consecutive uses; based on a first detected use of the respiratory medicament device, provide guidance by way of the instruction component to direct a second use of the respiratory medicament device according to a predetermined time schedule. Advantageously, the medicament sensor is able to monitor real time usage of a medicament device and provide guidance to the user using an onboard analysis module and instruction component. As such, the sensor itself is able to direct the correct timing of consecutive usage events without the need for connected client devices, applications or remote servers, although further analysis through such connections is also possible and often desirable.

The medication data may include information regarding at least one of a medicament type in use, a medicament device type in use, and a prescribed number of doses. For example, the medication data can include information on the period of time required between consecutive doses of a plurality of medicament types or medicament device types.

The predetermined time schedule may direct the second use of the respiratory medicament device after greater than 30 seconds following the first detected use.

The medicament sensor may further comprise a wireless transceiver to communicate with a mobile computing device.

The instruction component may be capable of providing audio and/or visual guidance to direct the second use of the respiratory medicament device.

In a further aspect, there is also provided a method comprising: accessing a set of historical rescue inhaler usage events for a patient, the set of events previously received from a client device or attachment (i.e. medicament sensor) associated with a rescue inhaler unit (i.e. medicament device) or from the rescue inhaler unit, the rescue inhaler unit having provided a rescue medication to the patient as part of each of the events and the set of historical rescue inhaler usage events including timestamps indicative of the usage timing; determining, based on the set of historical rescue inhaler usage events, timing between consecutive usage events for the patient; classifying the consecutive usage events as proper or improper technique based on the timing to generate a usage technique record; and generating notifications to a client device based on the usage technique record to enhance proper usage technique.

Notably, using such digital medicament device sensors to quantify the time between two administrations as a screening test for appropriate medication use technique, it has been detected that a high prevalence of errors in technique exists for most areas of the population. The present invention therefore provides an objective system for monitoring such improper timing technique and facilitates the learning and development of patients, caregivers and health providers in medication usage. As such, the present invention provides a system to identify, educate, train and monitor progress in the timing of medication administrations.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The disclosure will be better understood from the following description of exemplary embodiments together with reference to the accompanying drawings, in which.

Figure 1:
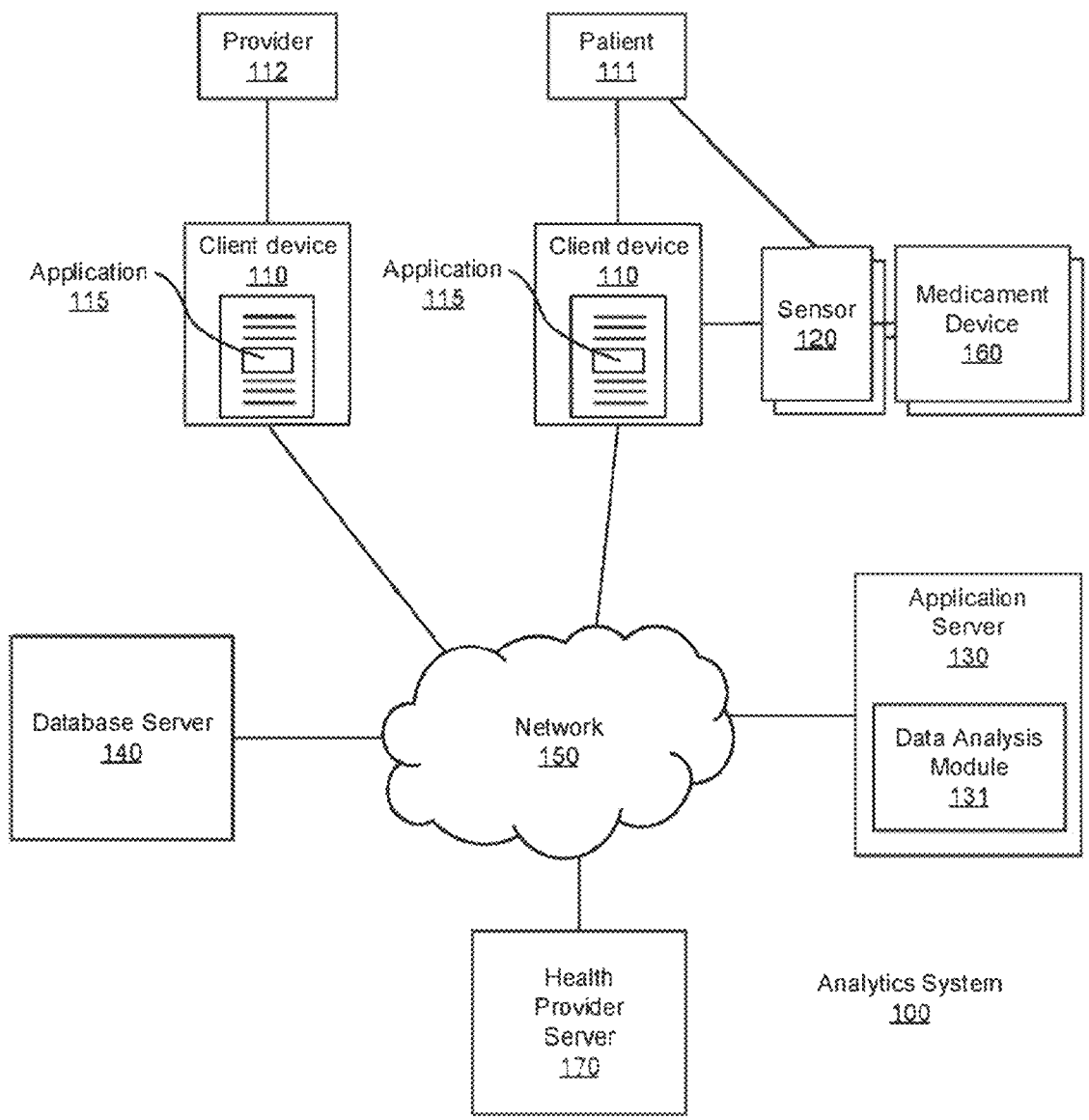
FIG. 1 shows a respiratory ailment analytics system for monitoring accurate, real-time medicament device usage, performing analytics on that data, and providing analysis of patients that may be subjects for enhanced treatment.

The present disclosure is susceptible to various modifications and alternative forms. Some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

The present invention can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

The present disclosure relates to a system that collects data relating to individual-level patterns of rescue inhaler use and controller medication adherence. The data may be used to identify and describe subgroups of patients with improper inhaler technique in terms of the timing of consecutive inhaler uses/puffs. Individual-level data is then used to provide notifications to the given individual (and/or their caregiver) to inform them of improper inhaler technique and educate them on how to improve their technique in order to satisfy proper technique and therefore maximize the efficacy of the medication(s). The data may also be used to identify subgroups of patients who are more susceptible to improper inhaler technique and provide notifications to such subgroups of patients based on which subgroup they fall into, e.g. subgroups based on age.

FIG. 1 shows a respiratory ailment analytics system 100 for monitoring accurate, real-time medicament device events, performing analytics on that data, and providing inhaler use technique notifications and/or respiratory ailment event risk notifications, according to one embodiment. Such respiratory ailments may be an asthma event or a COPD rescue event that may be addressed through prompt treatment of medicament through an inhaler.

The respiratory ailment analytics system includes client computing devices 110, a medicament device sensor 120, a medicament device 160, an application server 130, database server 140, and a network 150. Other servers, such as a health provider server 170, may be coupled to the network 150. Although FIG. 1 illustrates only a single instance of most of the components of the respiratory ailment analytics system 100, in practice more than one of each component may be present (e.g. multiple medicament device sensors 120 and/or medicament devices 160), and additional or fewer components may be used.

The client devices 110, at the behest of their users, interact with the respiratory ailment analytics system 100 via the network 150. For purposes of explanation and clarity it is useful to identify at least three different types of users. A patient 111 is a user burdened with a respiratory ailment such as asthma or COPD who makes use of the respiratory ailment analytics system 100 at least in part to obtain personalized notifications provided by the server 130, such as inhaler technique notifications and/or rescue event risk notifications, and management notifications created by their health care provider 112. The patient 111 may be supported by a caregiver who is an additional or alternative user. The caregiver may have their own application 115 and client device 110 which receives the same notifications as the patient 111 (not shown in FIG. 1), or receives notifications on the patient's behalf Such notifications can be provided in exchange for the user's permission to allow the respiratory ailment analytics system 100 to monitor the patient's 111 medicament device 160 usage. As will be explained below, medication events are detected by a sensor 120 associated with the medicament device 160 and the user's client device 110, which in turn reports to the application server 130, which in turn can initiate a process to generate inhaler use technique notifications and/or risk notifications which are provided to the user through the client device 110. Inhaler use technique notifications and/or risk notifications may also be generated by application 115 on the user's client device 110. In examples, the patients 111 may represent a patient population, for which individual data is taken for each patient in the group.

Another type of user is a healthcare provider 112 who, again with the patient's 111 express permission, also receives notifications regarding a patient's asthma or COPD management, as well as aggregated community rescue event data and derived statistics regarding events and other associated data. As noted above, other types of users are also contemplated, such as parents/guardians or other caregivers of patients 111 who may also want to receive notifications in the event that their own client devices 110 are distinct from that of the patient 111.

The client device 110 is a computer system that may be a portable computing device such as a smart phone, tablet, or laptop. The client device 110 could also be a television (e.g. a smart, connected television) or a speaker system (e.g. a smart, connected speaker). An example physical implementation is described more completely below with respect to FIG. 2. The client device 110 is configured to wirelessly communicate with the respiratory ailment analytics system 100 via network 150. With network 150 access, the client device 110 transmits to respiratory ailment analytics system 100 the time of medication usage events, as well as information describing the event as received from the associated medicament device sensor 120 (referred to throughout as "sensor 120"). The user's geographical location may also be transmitted to the respiratory ailment analytics system 100.

Regarding user location and event times, the client device 110 may determine the geographical location and time of an event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the respiratory ailment analytics system 100 may also exchange information with other connected client devices 110. For example, through a client software application 115, a healthcare provider 112 may receive inhaler usage and/or exacerbation risk notifications describing a recent rescue event about a patient 111, then in response send a recommendation to the patient 111 for post-asthma rescue event treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the respiratory ailment analytics system 100. For example, the dashboard allows patients 111 and providers 112 to interact with each other, receive inhaler usage and/or rescue event risk notifications, exchange messages about treatment, provide and receive additional event and non-event data, and so on. Application 115 may be coded as a web page, series of web pages, or content otherwise coded to render within an internet application. Application 115 may also be coded as a proprietary application configured to operate on the native operating system of the client device 110.

In addition to providing the dashboard, application 115 may also perform some data processing on asthma event data locally using the resources of client device 110 before sending the processed data through the network 150. Event data sent through the network 150 is received by the application server 130 where it is analyzed and processed for storage and retrieval in conjunction with database server 140. The application server 130 may direct retrieval and storage request to the database system as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicates information relating to medication device usage with the client device 110. If the sensor 120 has not been paired with a client device 110 prior to a rescue medication event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described herein as being separate physical devices (such as smart phones and inhalers, respectively), it is contemplated that the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation, the medicament device 160 itself may present the contents of notifications provided by the server 130 directly, in place of or in addition to presenting them through the client devices 110.

The medicament device 160 is a medical device used to deliver medication to the lungs of a user experiencing constricted respiratory airflow. Different medicaments may be used for asthma and COPD. Different medicaments may also be used for rescue and control for asthma and COPD. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline. Specific, branded examples of medicament devices requiring consecutive uses in accordance with the present invention include Ventolin, Proair, Proventil, Advair, Flovent HFA, Symbicort, Dulera, Qvar, and Asmanex HFA.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160. Each sensor 120 may be configured to log in its memory, from information sent via the associated application 115 and client device 110, the type of medicament device 160 (e.g. medication type, brand, and/or prescription) to which it is associated.

Generally, a sensor 120 is a physical device that monitors the usage of the medicament device 160. The sensor 120 is either removably attachable to the medicament device 160 without impeding the operation of the medication device dispenser 160, or the sensor 120 is an integrated component that is a native part of the medicament device 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or BTLE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time of the usage event, that is, usages of the medicament device 160, by the patient 111. A geographical location may be associated with the time of each usage event. Each sensor 120 transmits the event data in real-time or as soon as a network connection is achieved, automatically without input from the patient 111, caregiver or health provider 112. The medication event information is sent to the application server 130 for use in analysis, generation of asthma event notifications, and in aggregate analyses of event data across multiple patients. Analysis of the medication event information may also be conducted by application 115 of the client device 110.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

Figure 5:
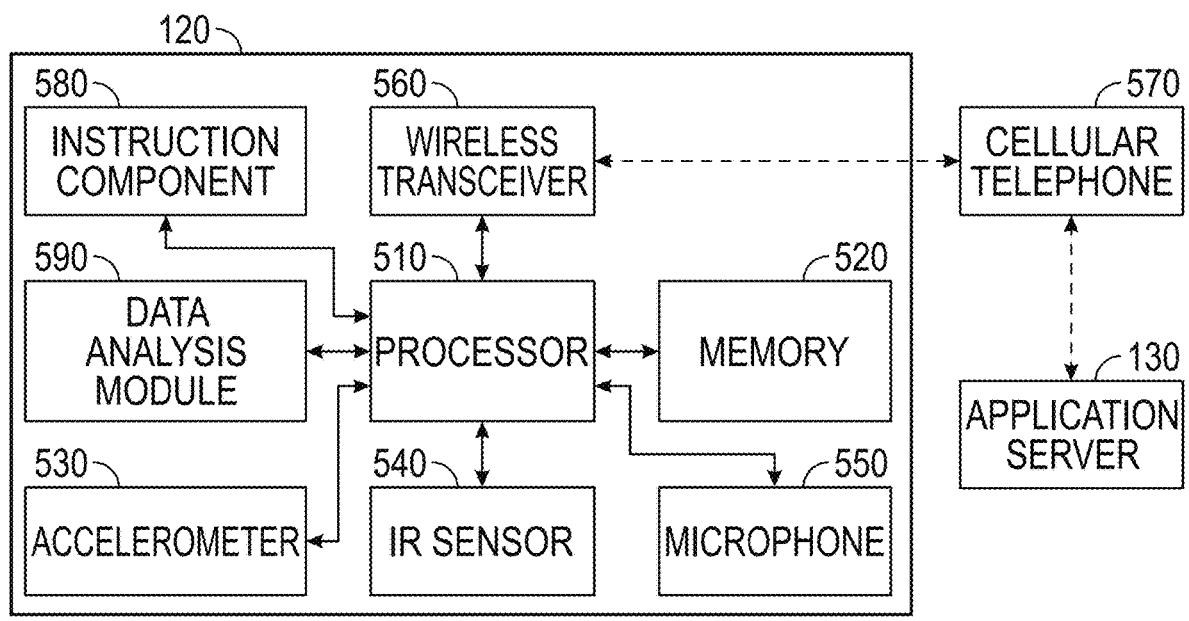
FIG. 5 is a block diagram of various components of a medicament device sensor according to one embodiment.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety. A specific implementation is depicted in FIG. 5, which is described further below.

Figure 2:
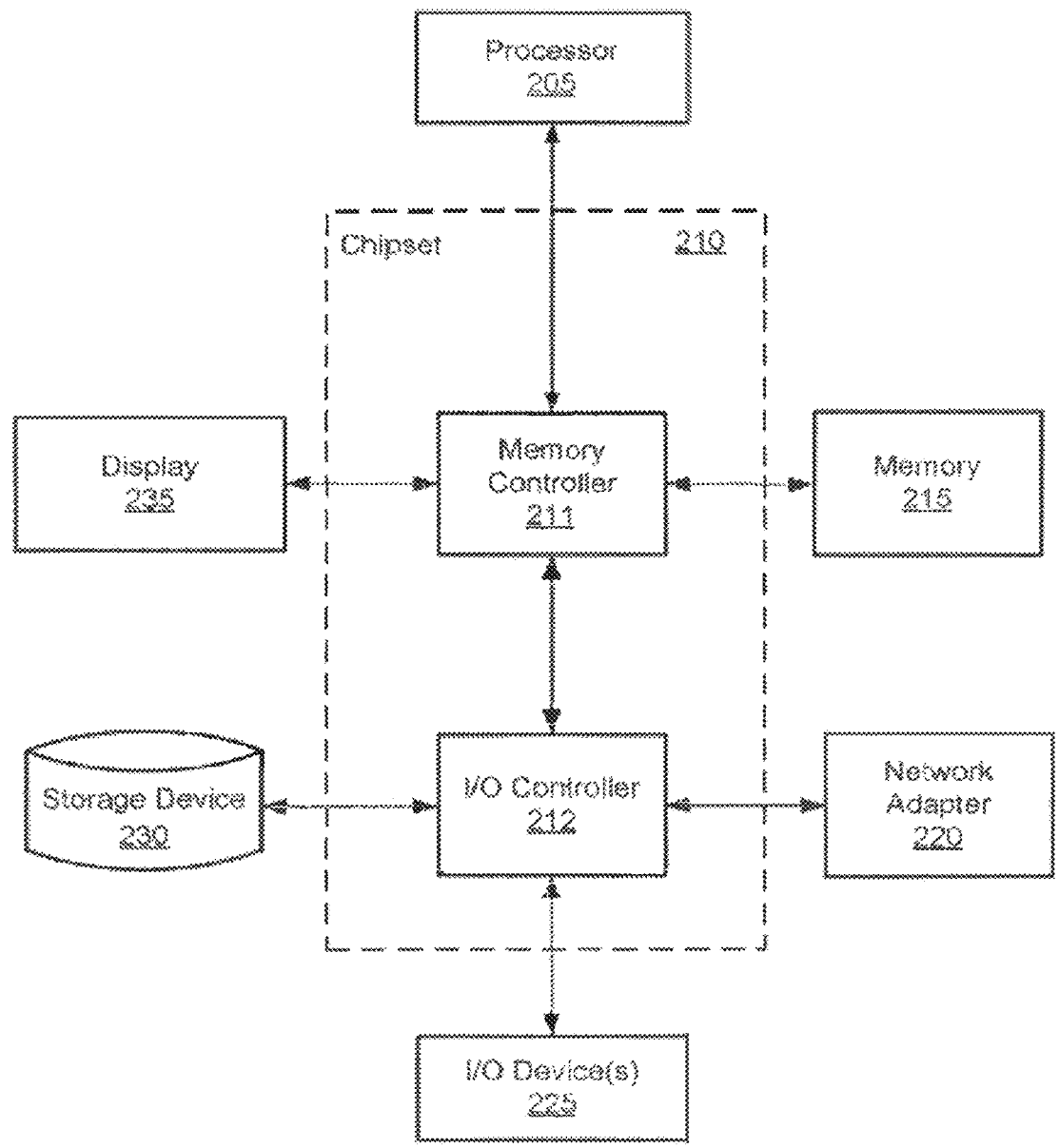
FIG. 2 is a high-level block diagram illustrating an example of a computing device used in either as a client device, application server, and/or database server.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use of the respiratory ailment analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on respiratory ailment treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the respiratory ailment analytics system 100. The patient profile may include identify information about the patient such as age, gender, current rescue medication, current controller medication, notification preferences, a controller medication adherence plan, a patient's relevant medical history, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111, their caregivers, and their personal healthcare providers 112, as well as the frequency with which notifications are provided. For example, a patient 111 may authorize a caregiver and/or a healthcare provider 112 to receive notifications indicating a medication event. The patient 111 may also authorize their caregiver and/or healthcare provider 112 be given access to their patient profile and medication event history. If the healthcare provider 112 is provided access to the patient profile of the patient 111, the healthcare provider may specify controller adherence or rescue medication plans for the corresponding COPD or asthma condition. Medication plans may include a prescribed number of doses per day.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives medication event information from the client device 110 or the sensor 120, triggering a variety of routines on the application server 130. In the example implementations described below, the data analysis module 131 executes routines to access respiratory ailment event data as well as other data including a patient's profile, analyze the data, and output the results of its analysis to both patients 111, caregivers and providers 112. This process is generally referred to as a respiratory ailment use analysis. In this example, the use analysis is performed in relation to asthma or COPD for the patient 111. The asthma or COPD use analysis may be performed at any point in time, in response to a medication event, due to a relevant change in the patient's environment, and in response to any one of a number of triggering conditions discussed further below.

Other analyses are also possible. For example, a use analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile, such as caregivers. Notifications can provide details about the timing, location, and affected patient(s) 111 involved in a medication use event. Notifications may also include the results of the respiratory ailment use analysis performed by the data analysis module 131. More information regarding the types of notifications that may be sent and the content they may contain is further described below.

In addition to providing push notifications in response to an asthma or COPD use analysis, notifications may also be provided as pull notifications, at particular time intervals. Additionally, some notifications (whether push or pull) may be triggered not in response to an asthma or COPD use analysis performed in response to a medication use event, but instead in response to a use analysis performed in response to one of the underlying factors in the asthma or COPD use analysis changing, such that an updated notification is warranted. For example, if weather conditions indicate that an increase in air pollution is occurring or is imminent, this may trigger the carrying out of asthma risk analyses for all patients located in the particular geographic area where the pollution is occurring.

Notifications can be provided through the network 150 to client applications 115 in a data format specifically designed for use with the client applications 115, and additionally or alternatively may be provided as short message service (SMS) messages, emails, phone calls, or in other data formats communicated using other communication mediums. In certain circumstances, notifications may be generated and provided by the client applications 115.

The database server 140 stores patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma use and/or risk analyses) that incorporate data from multiple patients (e.g., aggregate medication event data) and are provided to users is de-identified so that personally identifying information is removed to protect patient privacy.

The database server 140 also stores non-patient data used in asthma or COPD use analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the medication event such as temperature, humidity, air quality index. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130, the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

The contents of the databases may be stored in databases physically proximate to the application server 130 and separate from database server 140 as illustrated. Alternatively, those databases may be a part of database server 140. This and other variations thereupon are within the scope of this description.

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma or COPD analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

In this example, an application executed on the application server 130 may collect data such as use data from medicament devices such as the device 160 in FIG. 1. The application collects data from uses of medicament devices for patients and patient populations that can be used to determine improper medication (e.g. inhaler) use between consecutive doses. This may be confined to patients and patient populations on medication plans involving medication devices or combinations of different medication devices which require use in close succession.

For example, collected data may be used to determine factors such as: a) use of inhaled corticosteroids (ICS) or bronchodilator medicine such as LABA; b) proof of use of ICS/LABA; and proof of controller adherence. Additional inhaled corticosteroids data relating to asthma or COPD control may be analyzed. Such data relating to asthma may include inhaler usage, nighttime symptoms, an asthma control score (ACT), asthma control by ACT and external sensor readings such as spirometry readings. Such data relating to COPD may include inhaler usage, nighttime symptoms, and external sensor readings such as spirometry readings.

Underpinning the notion of improper medication usage according to consecutive medication administration timings, data has been analyzed from patients ≥4 years old with self-reported asthma (Anderson, W. C., Gondalia, R., Hoch, H. E., Kaye, L., Szefler, S. J., Stempel, D. A., Screening for inhalation technique errors with electronic medication monitors., J. Allergy Clin. Immunol. Pract., 2019, 7(6), 2065-2067). Their rescue and/or controller inhaler medicament devices had medicament device sensors (or EMMs) attached to determine the exact time and date of each actuation (+/−3 second error). Patients using two actuations within 120 seconds were included, as most consecutive actuations occur within this time period (Szefler, S. J., Hoch, H., Tuffli, M., Gondalia, R., Barrett, M. A., Van Sickle, D., Stempel, D. A., Quantifying beta agonist utilization: occasions or puffs?, J. Allergy Clin. Immunol. Pract., 2019; 7(3), 1088-1090). The interval between actuations was quantified and conservatively classified as acceptable (>30 seconds), fair (15 to ≤30 seconds), or poor (≤15 seconds) based on the available PILs and guideline criteria (National Heart Lung and Blood Institute, National Asthma Education and Prevention Program, Expert panel report 3: guidelines for the diagnosis and management of asthma, Full report 2007; Global Initiative for Asthma, Global Strategy for Asthma Management and Prevention, 2016, available from www.ginasthma.org). The change in the interval between actuations over time was assessed using the Akaike and Bayesian information criteria (AIC and BIC, respectively) and linear mixed effects models that allowed for within- and between-patient variability (Kuha, J., AIC and BIC: Comparisons of Assumptions and Performance., Sociol. Methods Res. [Internet]., 2004, 33, 188-229. Available from: https://doi.org/10.1177/0049124103262065). This study was determined as exempted from Institutional Review Board approval by the Copernicus Group IRB (PRH1-18-132).

The study data included 278,374 patient-days from 7,558 patients, of which 6,616 were rescue medication users on 120,882 patient-days, and 3,220 were controller medication users on 157,492 patient-days. The median (interquartile range) interval between actuations was 9 (16) seconds. It was found that 67% of multiple inhalations were separated by ≤15 seconds (poor), 17% by 15-30 seconds (fair), and 16% by >30 seconds (acceptable). The results were similar when stratified by rescue vs. controller and MDI vs. DPI use but varied by age. Patients 4-11 years had the highest level of "acceptable" inhaler use, while those 18-29 years had the lowest (22% vs. 14%, p<0.001). There was little variability in the interval between actuations over time within and between patients.

The data suggests that the majority of patients using inhaled medications are deficient in technique for both rescue and controller medications based on current device recommendations. A recent systematic review of HCP proficiency on using MDIs and dry powdered inhalers (DPIs) demonstrated that only 15.5% were using correct technique (Plaza, V., Giner, J., Rodrigo, G. J., Dolovich, M. B., Sanchis, J., Errors in the Use of Inhalers by Health Care Professionals: A Systematic Review., J. Allergy Clin. Immunol. Pract., 2018, 6, 987-95). The implications of these findings are that healthcare providers may not have the knowledge base, training or time to assure that the required steps of the medications are followed. Two common issues identified by Plaza et al. (ibid) were not exhaling completely and not breath-holding appropriately. Both parameters are detected by medicament device sensor 120-measured (or EMM-measured) duration between inhalations or inhaler actuations.

Levy et al. and Price et al. found inadequate inhalation technique was associated with decreased levels of asthma control (Levy, M. L., Hardwell, A., McKnight, E., Holmes, J., Asthma patients; inability to use a pressurised metered-dose inhaler (pMDI) correctly correlates with poor asthma control as defined by the Global Initiative for Asthma (GINA) strategy: a retrospective analysis., Prim. Care Respir. J., 2013, 22, 406) and increased exacerbations risk (Price, D. B., Román-Rodríguez, M., McQueen, R. B., Bosnic-Anticevich, S., Carter, V., Gruffydd-Jones, K., et al., Inhaler Errors in the CRITIKAL Study: Type, Frequency, and Association with Asthma Outcomes, J. Allergy Clin. Immunol. Pract. 2017, 5, 1071-1081.e9). The association of these critical errors and diminished outcomes demonstrates the importance of medication use technique. The use of medicament device sensors 120 (or EMMs) to assess the time taken to complete several of these parameters including preparing the device, exhalation, inhalation, and breath-holding therefore allows for a screen of appropriate technique in clinical practice.

Marketed inhalers for asthma contain PILs for rescue and controller medications, and the majority of rescue MDIs have comparable instructions. For example, GlaxoSmithKline and Merck MDI controllers have recommendations for 10-second breath-holding and a 30-second wait prior to the second inhalation. The Symbicort PIL does not have this wait time period, but as with the other MDIs a minimum of 30 seconds would be required between inhalations. Comparable recommendations are made for DPIs with the exception of shaking the device prior to use. Both US and global guidelines give recommendations that are consistent with the PILs, but less prescriptive on the specific times for these steps for inhalation (National Heart Lung and Blood Institute, National Asthma Education and Prevention Program, Expert panel report 3: guidelines for the diagnosis and management of asthma, Full report 2007; Global Initiative for Asthma, Global Strategy for Asthma Management and Prevention, 2016, available from www.ginasthma.org).

The use of medicament device sensors 120 (or EMMs) in screening for errors in inhalation technique can be limited in its specificity of several critical criteria for errors. Also, most prior studies have been performed in research environments where patients are more likely to be careful with their technique (Plaza, V., Giner, J., Rodrigo, G. J., Dolovich, M. B., Sanchis, J., Errors in the Use of Inhalers by Health Care Professionals: A Systematic Review, J. Allergy Clin. Immunol. Pract., 2018, 6, 987-95; Sanchis, J., Gich, I., Pedersen, S., Systematic Review of Errors in Inhaler Use: Has Patient Technique Improved Over Time?, Chest, 2016, 150, 394-406). However, medicament device sensors 120 (or EMMs) objectively and longitudinally measure temporal parameters related to medication use in the real world and have the ability to electronically deliver these daily observations to patients and providers. This demonstrates the value of medicament device sensor 120-derived (or EMM-derived) measurements to screen for errors in inhalation technique. The better technique observed in younger children compared to adolescents suggests the need for greater parental supervision, especially for adolescents. The large frequency of timing errors that were observed (less than 15% have an acceptable duration between consecutive inhalations) indicates the critical need for patient-level retraining and observation of medication use.

This study digitally screened for errors in inhalation technique by quantifying the time between two consecutive inhalations recorded by medicament device sensors 120 (or EMMs). It shows that objective monitoring helps identify patients who have inadequate parameters of technique that can limit the effectiveness of treatment and increase cost through higher medication use (Lewis, A., Torvinen, S., Dekhuijzen, P. N. R., Chrystyn, H., Watson, A. T., Blackney, M., et al., The economic burden of asthma and chronic obstructive pulmonary disease and the impact of poor inhalation technique with commonly prescribed dry powder inhalers in three European countries. *BMC Health Serv. Res.*, 2016, 16, 251). Digital application-based interventions that rapidly disseminate educational instructions and target at-risk subgroups and/or their providers therefore allow for efficient, cost-effective, and scalable solutions to counter widespread misuse of inhaler medication (Price, D., Bosnic-Anticevich, S., Briggs, A., Chrystyn, H., Rand, C., Scheuch, G., et al., Inhaler competence in asthma: Common errors, barriers to use and recommended solutions, *Respir. Med.*, 2013, 107, 37-46). Healthcare providers and pharmacists should also emphasize and evaluate inhalation technique before prescribing and dispensing medications, respectively.

As previously explained, medication use events are detected by a sensor 120 associated with the medicament device 160 and the user's client device 110. This allows monitoring and review of individual level medicament use timings. Furthermore, each patient 111 usually has a specific medication plan listed in their patient profile, as created by the application server 130, that specifies medication type, brand, prescribed number of uses/puffs and times per day. For each medication listed in the medication plan, the respiratory ailment analytics system 100 can automatically retrieve information from the medication manufacturer's website about recommended dosage and timing ("package insert" information or PILs). The respiratory ailment analytics system 100 can identify which medication requires at least two consecutive puffs, and therefore is relevant for timing monitoring or review. This information may be customized by region or country where the respiratory ailment analytics system 100 determines that users are susceptible to improper inhaler usage. This process may occur for both rescue and controller medications, as appropriate. Information regarding the medication plan and/or medication type may be stored by the application server 130, the client device 110, and/or the sensor 120.

The respiratory ailment analytics system 100 identifies the timing between consecutive medication uses, e.g. inhaler actuations (puffs). Consecutive medication uses may be defined as two administrations occurring within a predetermined time limit, such as 120 seconds. Consecutive administrations occurring outside this predetermined time limit, e.g. separated by greater than 120 seconds, may not regarded as consecutive for the purpose of monitoring proper or improper medication device use.

Monitoring and review of medication usage events by sensor 120, and thus the timing of consecutive medication administrations, may be conducted by the data analysis module 131 of the application server 130. This may occur as soon as the data relating to the medication usage events is transmitted to the application server 130. Alternatively, the monitoring and review may be conducted on the client application 115 of the client device 110. This may occur as soon as the data relating to the medication usage events is transmitted to the client device 110. In each case, the transmission of medication usage event data may occur in real time, i.e. immediately, or be delayed until the relevant components of the analytics system 100 are in communication. Similarly, analysis of the medication usage events may be conducted immediately or historically.

Following collection of medication usage events by sensor 120, the respiratory ailment analytics system 100 identifies if the associated medicament device 160 requires multiple, e.g. at least two, consecutive administrations, such that a review of the timing between administrations is required. It then identifies consecutive events and classifies them as being "proper" or "improper." Consecutive events may be defined as proper (or "acceptable") if they are separated by at least a predetermined time frame, such as greater than 30 seconds. Conversely, medication usage events may be defined as improper if consecutive events are not separated by at least a predetermined time frame, such as less than or equal to 30 seconds. Such improper events may further be classified as "poor" if the consecutive events occur within 15 seconds of each other, or "fair" if the consecutive events occur from 15 to 30 seconds of each other. This is detailed in the specific study example underpinning the invention as described above.

The collected data may also be analyzed by the respiratory ailment analytics system 100 to quantify the occurrences of consecutive events falling into specific categories. For example, the occurrences of controller inhaler usage, rescue inhaler usage, MDI usage, DPI usage, and demographic categories of users, such as age and location. The respiratory ailment analytics system 100 may then provide comparisons of usage at the population level. Analyses may also be customized by geographical region, such as country, state, or local region.

The data collected by respiratory ailment analytics system 100 may be accessible to the patient, health provider and caregiver in the client application 115 and/or a web-based dashboard. A flag may be placed on each medication use that was inappropriately timed, i.e. determined as being improper. This may be visible in a "timeline view" in the application 115 and/or web-based dashboard, such that the patient's entire medication use history can be accessed and reviewed.

Accordingly, the respiratory ailment analytics system 100 enhances therapeutic efficacy of administered medication. Particularly, the respiratory ailment analytics systems 100 receives timestamped usage events for patients and can process these events to detect relative timing between usage. The timing can be analyzed to detect instances of proper and improper usage and these instances can be further tracked by the respiratory ailment analytics system 100 for an individual patient and across a population of patients. The analytics system 100 may also be configured to determine the change in a user's timing parameters of consecutive medication administrations, thereby facilitating the ability to monitor and review a user's improvement or deterioration in technique over time. Notifications in this regard may be sent to the patient 111 (and/or the patient's caregiver) or health provider 112 as a means to discourage continued improper use, or to provide positive reinforcement for improvements in technique, depending on the user's change over time.

The respiratory ailment analytics system 100 can automatically generate notifications to patients based on their respective usage patterns in order to encourage proper usage. Similarly, notifications may be generated to caregivers (e.g. parents, partners, etc.), and/or healthcare providers, either alternatively or in addition to patients. Such notifications may be delivered by text, SMS, email, push notifications, or within application 115 of the client device 110. The notifications may be triggered by at least one identification of improper use involving consecutive medication administrations. Alternatively, the notifications may be triggered by at least 2 or 3 consistent identifications of improper medication administrations. Such multiple consistent identifications may be within a predetermined time period, such as a week. Notifications may be sent to the user immediately or on a predetermined time schedule, such as a particular time of day. Once the user has been notified once of improper inhaler use, subsequent improper use triggering may only be notified on a given time schedule, such as once per week.

The analytics system 100 can push notifications to client devices 110 that include alerts about the patient's usage and may include video and/or other educational content encouraging proper usage tailored to the particular type of medication type and/or medicament device 160 form factor. Educational materials may form part of an educational content module. Educational materials may be stored on application 115 of the client device 110 and/or on the application server 130.

The educational material may be delivered to application 115 of the client device 110 as one or more interfaces that indicate the importance of timing in the administration of consecutive medication uses, and optionally the associated potential benefit to the patient 111. The one or more interfaces may walk the user through the steps involved in employing proper medication use technique. Educational material may also be provided to healthcare providers and/or caregivers for training or refresher purposes, and may be accessible for use while the patient is in clinic.

Figure 3:
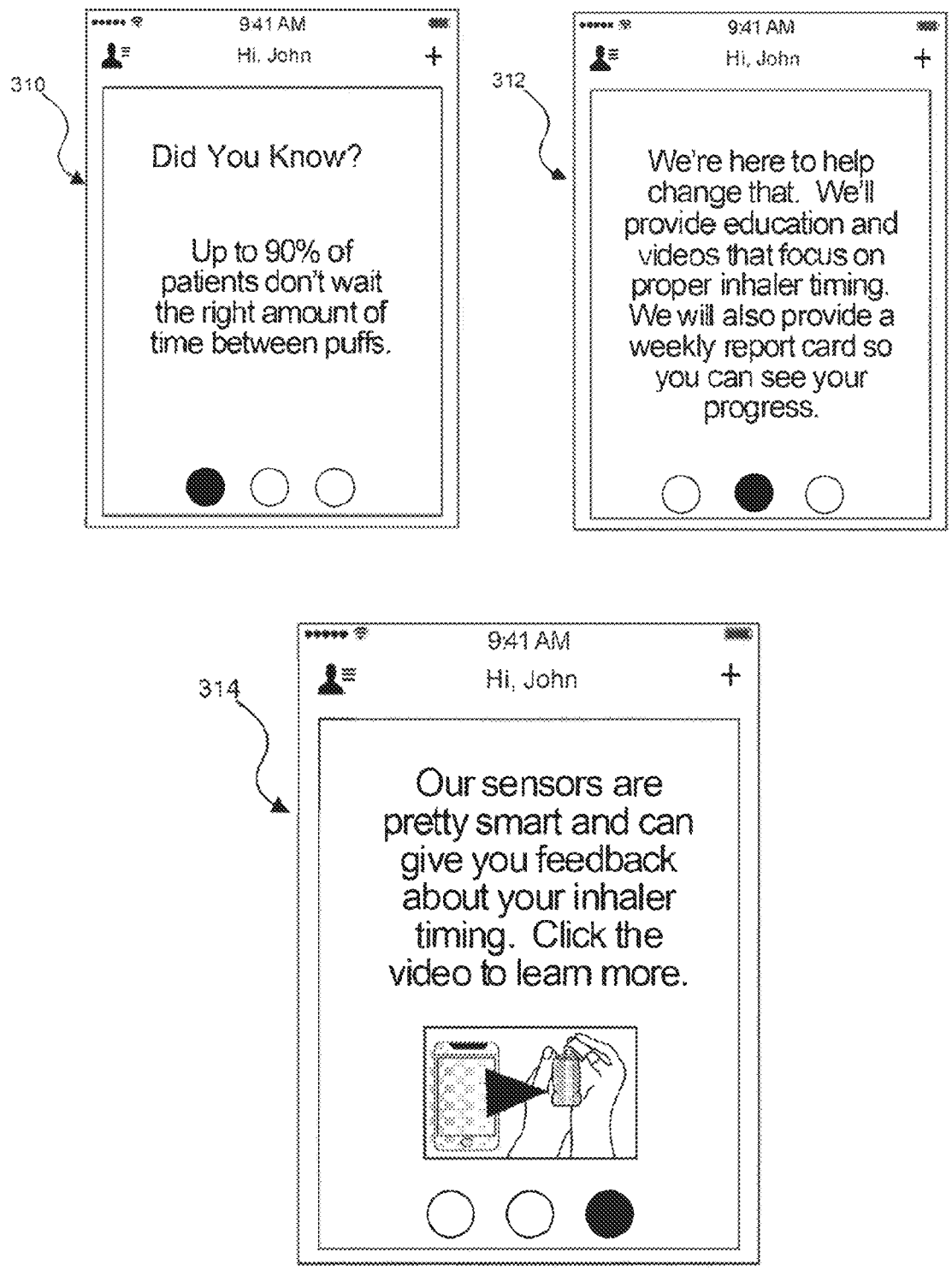
FIG. 3 shows screen images of interfaces generated by an example application that may be created and executed on a patient computing device to educate the patient in proper medication usage.

For example, FIG. 3 shows screen images of interfaces generated by an example application 115 executed on the client device 110. Interfaces 310, 312, 314 respectively highlight the issue of improper inhaler timing, providing reassurance that the system is monitoring for such improper technique, and linking educational material to teach the user about how the sensor works and/or how to use the inhaler in an effective and proper manner. These types of interfaces may be delivered to individual users in response to detected improper inhaler use, or may be delivered to specific groups of patients, either preemptively, simultaneously or periodically, who have been identified as groups showing a significant level of improper inhaler use based on the patient population. Interfaces 312-314 may be delivered to a user as part of the series 312-314, on their own, or in any combination. The educational content linked to interface 314 may be specific to the particular inhaler in use by a given user, information on which forms part of the patient profile. Similarly, the application 115 may directly link the patient 111 to video content on appropriate inhaler technique specific to the particular inhaler identified in their profile, such that no input is required by the patient 111 to prompt educational content. Such educational content may also be available within application 115 for access by the patient 115 at any time.

Notifications regarding medication usage are sent to the application 115 of the client device 110 (associated with the patient 111, their caregiver, and/or provider 112). Notifications may be immediate or delayed according to a predetermined time schedule, such as five minutes after the medication usage event, or at a particular time on a daily, weekly or monthly basis. Notifications inform the user that the medication usage based on consecutive administrations is either proper or improper. If the respiratory ailment analytics system 100 is determining that the patient 111 has adopted proper technique, a notification may not be triggered. Additionally, notifications may be collated into a daily, weekly or monthly report on the patient's usage characteristics. Such a report may be delivered to the patient 111 and/or provider 112. The notification may make suggestions on how to improve medication use technique and/or include individual statistics on the patient's usage characteristics, e.g., "we noticed you may not have waited long enough in between inhalations . . . try this timer next time . . . ," (see, also, interface 412 of FIG. 4) or to encourage when improvement has been observed, e.g., "98% of your doses this week were taken with the correct timing."

Figure 4:
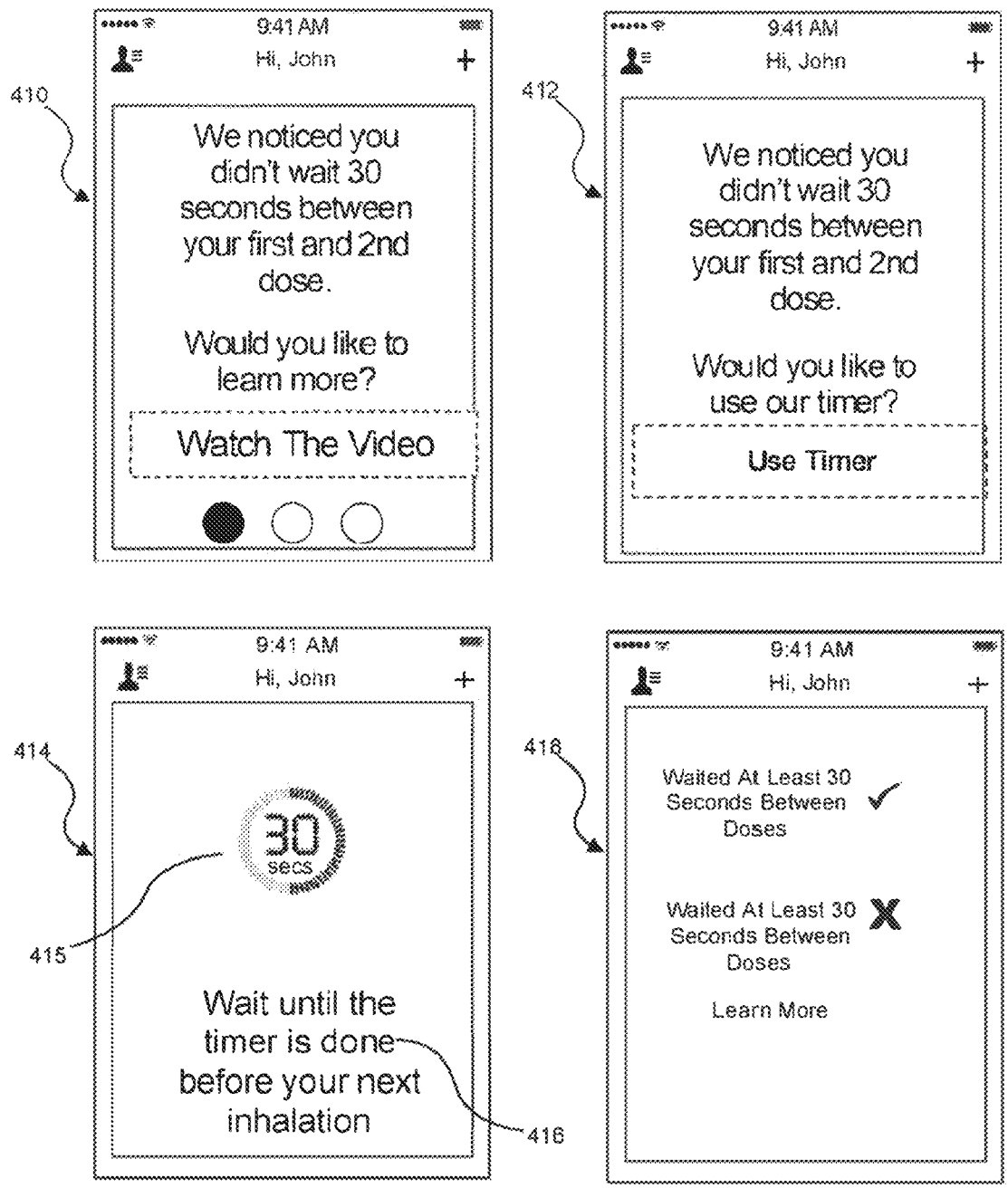
FIG. 4 shows screen images of interfaces generated by an example application that may be created and executed on a patient computing device to assist the patient with employing proper medication usage.

For example, FIG. 4 shows screen images of interfaces generated by an example application 115 executed on the patient computing device 110. Interfaces 410, 412 may be sent as notifications in response to improper medicament device technique as identified by respiratory ailment analytics system 100. Interface 410 shows a general notification highlighting improper timing between consecutive administrations, and links to general education material regarding proper technique. As noted herein, such educational material may be specific to the particular inhaler in use by the given user, information on which forms part of the patient profile. Alternatively, interface 412 links to a timer configured to assist the patient with waiting the recommended length of time between consecutive administrations, which is set out for the specific medicament device 160 in the respective PIL. The timer may be configured to indicate at least 30 seconds of time between consecutive administrations. Interface 414 shows a visual timer 415 and message 416 to inform the patient of the required time delay from the first administration, such that the patient can then proceed with the second administration in a proper manner. The interface 414 may change upon completion of the timed period to then provide the patient with a message stating that the second administration may then be completed.

The timer exemplified in interface 414 may be initiated in application 115 of the client device 110 manually by the patient, i.e. at the time of the first administration, or may be triggered and displayed automatically in response to the sensing of an administration by the sensor 120 for a patient on a treatment plan requiring consecutive medicament administrations.

In another example, an interface may be initiated in application 115 in response to the sensing of an administration of medicament by sensor 120, wherein the interface provides audiovisual content as a demonstration of proper medicament use in real time, e.g. a video of a person exhibiting proper medicament timing and technique for the specific device in use. The user can use this content as a guide and copy the timing and technique. The interface may also include a timer as indication to the patient of the required timing between administrations.

In a further implementation, an interface may be initiated in application 115 in response to the sensing of an administration of medicament by sensor 120, wherein the interface provides an augmented reality construct using a camera associated with the client device 110 to display the patient 111 taking their medication and assist with proper timing and technique. The augmented reality construct may include a display of the patient 111 with their specific medication together with guidelines on next steps to ensure proper usage of the medicament device. The guidelines may include arrows, written content, augmented images, mirrored images, and/or verbal content. The construct may also include a timer.

Interface 418 is a screen image of an exemplary report showing multiple medication usage events over a predetermined time period. It identifies historical usage events which have been classified as improper or proper depending on the timing between consecutive administrations of medication. Where improper technique has been identified, links to further information and/or educational content may be included in order to assist with technique coaching. Such reports may be delivered to the patient 112, caregiver and/or the health provider 112 via the application 115 of the client device 110. These reports may be readily accessible on request by the user, or may be delivered on a predetermined time schedule, such as weekly or monthly. Such reports may give an insight into the change in medication use over time, and therefore be used for personalized feedback on medication use technique. The dates and times of the usage events may be included in the report. Scores may be applied to the individual usage events to identify the relative quality of the usage event in terms of timing technique.

Other types of interfaces may introduce gamification concepts to the application 115. For example, interfaces may include comments of encouragement to promote proper usage, and/or incentives to achieve proper usage. Incentives may include rewards for proper usage.

The present invention also contemplates a sensor 120 facilitating automatic recognition of medication usage timing for medicament devices 160 requiring multiple consecutive administration. Specifically, medication usage timings can be evaluated in real time either on the sensor 120 alone, or by the combination of the sensor 120 and the application 115 of the client device 110. For example, as noted herein, the sensor 120 can sense the administration of a medication dose and, for medicament devices 160 requiring consecutive administration, communicate with the application 115 of the client device 110 to notify the user that a predetermined time period, such as 30 seconds, should be allowed to elapse before a second administration is performed. This could be implemented by a visual timer, such as that depicted as interface 414 in FIG. 4, or by an audio sequence, such as a series of beeps or verbal commands, in order to direct the patient 111 into proper medication usage. Alternatively, the sensor 120 may be configured to achieve this alone, as described below in relation to FIG. 5.

FIG. 5 is a block diagram of various components of a sensor 120 according to a specific implementation of the present invention. The sensor 120 includes a processor 510 which controls its operation. In various constructions, the processor 510 can include a microcontroller, microprocessor, ASIC, or other circuitry. However, in this particular example, the processor 510 accesses software instructions stored on a memory 520 and executes the instructions to control the operation of the sensor 120. The memory 520 can include, for example, one or more transitory or non-transitory memory components such as random access memory ("RAM"), read-only memory ("ROM"), flash memory, and other magnetic memory media. In this example, the memory module 520 includes a non-volatile memory that retains stored data when power is lost (or intentionally removed).

In this embodiment, the processor 510 is connected to three sensor modules—an accelerometer 530, an IR sensor module 540, and a microphone 550. The accelerometer 530 measures accelerations applied to the sensor 120 caused by movements of the medicament device 160. Furthermore, the accelerometer 530 may be positioned and configured to detect an impulse caused by the movement of a priming lever. The accelerometer 530 includes a low-power, 3-axis accelerometer that is being monitored at all times. Alternatively, the sensor may include one or more capacitive sensors to detect when the device is being handled.

The IR sensor module 540 includes a pair of infrared sensors. The IR sensors are positioned to monitor movements of the device body of the medicament device 160 and to indicate whether the device 160 is an administration-ready position or not. Although the examples described herein include an IR sensor module, some alternative constructions will include other sensor mechanisms to determine whether a device 160 is used and/or in an administration-ready position or not. For example, a mechanical switch or magnetic detection can be used to detect movement of the device body, or relative movement of the sensor 120 compared to the device 160.

Alternatively, the sensor housing itself can be constructed of a metalized plastic material or with electrodes which would allow the entire body of the attachment device to operate as a capacitive sensor. Changes in capacitance could be monitored to indicate when the device is being handled, thereby also replacing the accelerometer. In addition, the electrodes can sense when the patient lips are near or contacting the mouthpiece.

The microphone 550 captures audio of the patient inhaling the medication. This audio data is processed by the processor 510 or by the external analytics system 100 to ensure appropriate medication usage. Furthermore, the microphone system 550 is configured to identify, note, and segregate inhalation events from other background noise. The microphone system 550 eventually adapts to eliminate false positives by recognizing an audio signal that is associated with a user's unique inhalation. As the microphone system 550 is able to adapt based on "learned" data, the accuracy of the attachment device and its ability to correctly identify inhalation events is improved. Alternatively, or in addition to, microphone 550, a barometric pressure sensor may be included to sense pressure changes associated with inhalation events. For example, a barometric pressure sensor can identify when the patient 111 inhales and/or exhales during usage of the medicament device 160, thereby providing information on the timing, length and/or strength of inhalation and/or exhalation.

The processor 510 is also connected to a wireless transceiver 560 that is configured to exchange data with the client device 110. In the example of FIG. 5, the wireless transceiver 560 communicates with a cellular telephone 570 carried by the user (i.e. the cellular telephone 570 is the client device 110). The cellular telephone 570 further relays information between the sensor 120 and the application server 130. The wireless transceiver in this example is a BTLE transceiver. However, other constructions may include any other type of wireless communication device including, for example, Wi-Fi, cellular, or RF transceivers.

The example of FIG. 5 shows the accelerometer 530, IR sensor module 540, microphone 550, and wireless transceiver 560 all directly connected to the processor 510. However, it is to be understood that the sensor 120 may include a controller area network ("CAN") with a bus for relaying data between the various components of the sensor 120. Other configurations and communication mechanisms are also possible.

Furthermore, although the example of FIG. 5 shows communication with the application server 130 through a wireless relay with a cellular telephone 570 carried by the patient 111, other constructions may include other mechanisms for transferring data between the sensor 120 and the application server 130. For example, the sensor 120 may be equipped with a cellular communication module for directly communicating with the application server 130 over a cellular telephone network. Alternatively, the sensor 120 may include a Wi-Fi transceiver for communicating with the application server 130 through the internet or other computer network.

In the example of FIG. 5, the processor 510 may be configured to detect and identify administrations of medicaments required to be administered on a consecutive basis according to the medicament's PIL and/or the patient's treatment plan. As noted herein, this may be specified in the patient profile, and stored in the memory 520 of the sensor 120. In this connection, the sensor 120 may also include a data analysis module 590 which is operable to determine, based on medication data associated with the patient's profile, whether the medicament device 160 in use by the patient requires a plurality of consecutive uses, and provide guidance by way of an instruction component 580 to direct a second use of the medicament device 160 according to a predetermined time schedule. For example, the instruction component 580 may be configured to either emit an audio sequence or a visual indication that directs the patient 111 into proper medication usage. In one example, an audio sequence (e.g. a series of beeps or verbal commands) may be emitted by a speaker (not shown in FIG. 5) to signify when the required time period has elapsed between consecutive administrations. Additionally or alternatively, a visual indication may be displayed by a screen or light, such as a flashing light-emitting diode, to indicate to the patient 111 when the required time period has elapsed between consecutive administrations.

Figure 6:
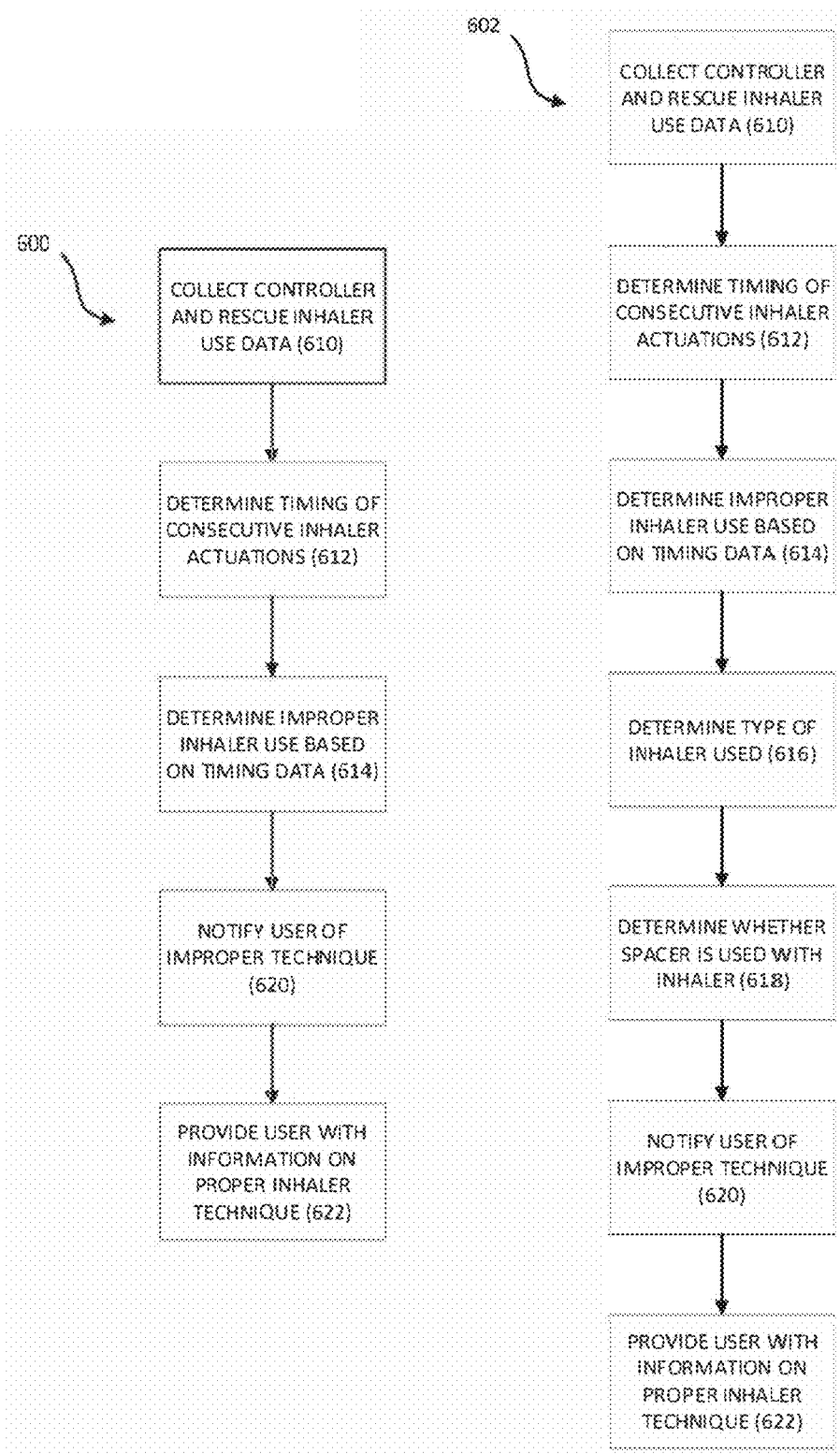
FIG. 6 depicts flow diagrams of data collection and analysis routines to determine proper or improper medication usage and inform a user thereof.

FIG. 6 shows two flow diagrams 600, 602 of data collection and analysis routines to determine proper or improper medication usage and inform a user (i.e. patient 111, caregiver and/or health provider 112) thereof, according to certain aspects of the present disclosure. The flow diagrams in FIG. 6 are representative examples of machine readable instructions for the process of collecting data, determining proper or improper medication usage and notifying a user accordingly in order to maintain proper usage or direct proper usage. In these examples, the machine readable instructions comprise an algorithm for execution by: (a) a processor; (b) a controller; and/or (c) one or more other suitable processing device(s). The algorithm may be embodied in software stored on tangible media such as flash memory, CD-ROM, floppy disk, hard drive, digital video (versatile) disk (DVD), or other memory devices. However, persons of ordinary skill in the art will readily appreciate that the entire algorithm and/or parts thereof can alternatively be executed by a device other than a processor and/or embodied in firmware or dedicated hardware in a well-known manner (e.g., it may be implemented by an application specific integrated circuit (ASIC), a programmable logic device (PLD), a field programmable logic device (FPLD), a field programmable gate array (FPGA), discrete logic, etc.). For example, any or all of the components of the interfaces can be implemented by software, hardware, and/or firmware. Also, some or all of the machine readable instructions represented by the flowcharts may be implemented manually. Further, although the example algorithms are described with reference to the flowcharts illustrated in FIG. 6, persons of ordinary skill in the art will readily appreciate that many other methods of implementing the example machine readable instructions may alternatively be used. For example, the order of execution of the blocks may be changed, and/or some of the blocks described may be changed, eliminated, or combined.

The routine 600 first collects controller and rescue use data associated with a patient using a respiratory medication (610). As noted herein, the use data may be collected immediately after medication usage (i.e. in real time) or delayed according to a predetermined time schedule, such as five minutes after medication usage, or at a particular time on a daily, weekly or monthly basis. The routine 600 then determines the timing of consecutive inhaler actuations (612), whereby consecutive inhaler actuations are as defined above, i.e. neighboring actuations occurring within a predetermined period of time such as 120 seconds. The routine 600 may make this determination only for patient's using inhaler types requiring multiple administrations, as identified in the patient's profile. As such, an additional block in the routine (not shown in routine 600) is a determination of whether the specific inhaler in use requires an analysis of such proper or improper usage, i.e., is an inhaler where a plurality of consecutive uses is expected.

This collection of data may also able be conducted on a general population of patients that use respiratory medications for the purpose of analyzing population trends in medication usage techniques. Population level data may be collected periodically over a period of time, such as weekly, monthly, quarterly or annually. As such, the routine 612 may facilitate a determination of patterns of improper inhaler technique.

The routine 600 then examines the timing of consecutive inhaler actuations and determines whether the patient 111 has employed proper or improper inhaler usage (614). In this example, improper usage may be defined as consecutive inhaler actuations separated by less than or equal to 30 seconds, and proper usage as consecutive inhaler actuations separated by over 30 seconds. If the routine 600 determines improper usage (614), a notification is sent to the user, such as via the application 115 of the client device 110, in order to inform the user that the inhaler has been used improperly (620). Additionally or alternatively, notifications may be sent to the health provider 112 such that medication usage technique can be monitored and addressed by trained professionals, as described herein.

The notification or notifications may include any of the educational content described in detail herein, and may assist the patient 111 in adopting proper technique, such as by coaching the patient 111 to wait for over 30 seconds. As such, the routine 600 provides the patient 111 with information on proper inhaler technique (622). Additional relevant medical data may also be retrieved for association with the patient 111 for use in the routine 600.

In one example, the patient notification of improper technique (620) and information on proper inhaler technique (622) comprises assisting the patient to adhere to the required timing between consecutive inhaler actuations, such as with the timer application and/or audiovisual guidance implementations described in detail above.

The routine 602 shares the same blocks and considerations as routine 600. In addition, routine 602 includes further blocks in order to provide individualized care to the patient 111, and/or provide inhaler specific feedback to the health provider 112, pharmacist and/or medication manufacturer. Specifically, routine 602 determines the type of inhaler used (616) by the patient 111, and whether a spacer is used with the inhaler (618). This information may be retrieved from the patient profile, which may be stored in memory on the application server 130, the client device 110, or the sensor 120. The determination of the type of inhaler used (618) allows the routine 602 to determine proper or improper inhaler use based on that given inhaler (e.g. according to the instructions set out in the inhaler PIL) and provide feedback appropriate for that inhaler. Similarly, the determination of whether a spacer is used (618) allows a consideration of whether the timing determination of proper and improper use should be modified, and/or specific feedback should be given according to the inhaler and spacer being used. As such, personalized feedback can be provided based on the patient's individual inhaler usage.

In another implementation, as noted above, the application 115 of the client device 110 may be configured to allow the patient 111 or caregiver to schedule a consultation regarding inhaler usage technique with provider 112 or a respiratory therapist. The consultation may be in person, via telephone or via videoconference. Such a consultation may be scheduled manually by the patient 111, caregiver or health provider 112, or automatically by the analytics system 100. This allows immediate and personalized feedback on inhaler technique.

The analytics system 100 may monitor the ongoing metrics of improper inhaler timings and associated feedback. As such, the analytics system 100 may be configured to monitor and compare inhaler usage and associated interventions over time. In this case, if initiated interventions (e.g. application-based training) do not result in an improvement of inhaler technique, additional and more thorough and intensive interventions (e.g. virtual or actual meetings) may be recommended and/or scheduled. As such, the respiratory ailment analytics system 100 may provide access to one-on-one virtual tutoring (e.g., via voice or video conference) for patients identified as demonstrating a pattern of improper technique.

The respiratory ailment analytics system 100 can additionally generate notifications to health providers 112 that may include suggestions for outreach to patients regarding proper usage. For example, the respiratory ailment analytics system 100 may identify patients 111 in the population that should receive education relating to their usage technique at their next visits.

Data collected and analyzed by the analytics system 100 concerning the inhaler usage of patients may be presented in a provider dashboard. Improper inhaler usage may be flagged in the provider dashboard for a given patient 111 as part of their patient profile. Furthermore, notifications may be sent to the provider 112 for patients exhibiting consistent improper inhaler use, which may be triggered by a particular threshold of consistent improper use, e.g. a given percentage of consecutive actuations taken improperly, such as at least 50%, 60%, 70% or 80%. This may be within a specific period of time, such as a week or month. The provider 112 may be notified immediately or as part of a periodic report, such as weekly or monthly. Based on the collected data, recommendations may be made to the provider 112 in order to assist with improving inhaler technique. For example, the provider dashboard may provide a link to the specific inhaler used by the patient 111, as set out in the patient profile.

In another embodiment, the respiratory ailment analytics system 100 may provide aggregated, de-identified feedback for specific medications and inhaler form factors. This feedback may include, for example, analytics on the percentage of patients applying proper or improper usage, the types of patients that are susceptible to improper usage, and/or duration of the timing error(s). This information may be used to inform on future drug and/or inhaler device development.

In another embodiment, the respiratory ailment analytics system 100 may provide information to pharmacists on how to educate patients picking up their prescription based on learned usage trends, and common errors identified for specific inhaler types (e.g. pMDI vs. DPI) and brands.

In another embodiment, the respiratory ailment analytics system 100 may provide aggregated, de-identified feedback for specific medications and inhaler form factors to payors for patient education needs by medication type. This feedback may include, for example, analytics on the percentage of patients applying proper or improper usage, the types of patients that are susceptible to improper usage, and/or duration of the timing error(s). This information may be used to inform provider and pharmacist education.

The data collected and analyzed by analytics system 100 may be used to link proper or improper inhaler timing to other inhaler usage traits, such as adherence to the patient's medication plan. This may facilitate a further dimension to assessing a patient's control of their condition, and whether they are likely to experience future exacerbations of their condition.

Although the discussion above may focus on asthma specifically, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used in this application, the terms "component," "module," "system," or the like, generally refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer.

By way of illustration, both an application running on a controller, as well as the controller, can be a component. One or more components may reside within a process and/or thread of execution, and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

The invention claimed is:

1. A method of ensuring proper usage technique of a respiratory medicament device for a respiratory ailment, the method comprising:
   collecting, by at least one processor associated with the respiratory medicament device, medication data relating to a medication plan for a patient, the medication data including at least one of a type of the respiratory medicament device and a prescribed number of doses of a respiratory medicament associated with the respiratory medicament device;
   based on the medication data, determining whether the respiratory medicament device requires a plurality of consecutive uses;
   based on determining the respiratory medicament device requires a plurality of consecutive uses, determining a timing between consecutive uses of the respiratory medicament device;
   based on determining a spacer is used with the respiratory medicament device, determining a modification to the timing between the consecutive uses;
   detecting, by a medicament sensor associated with the respiratory medicament device, a first set of use data of the respiratory medicament device, the first set of use data including at least a first inhalation event associated with the patient;
   identifying, from the first set of use data, a usage characteristic associated with the patient, the usage characteristic including an audio signal associated with an inhalation of the patient;
   applying an adjustment to the medicament sensor in response to identifying the usage characteristic, the adjustment causing the medicament sensor to eliminate false positives in response to detecting a second set of use data, the second set of use data including at least a second inhalation event associated with the patient;
   detecting, by the medicament sensor, the second set of use data;
   identifying, from the second set of use data, the second inhalation event; and
   based on identifying the second inhalation event, providing a guidance by way of an instruction component to direct a subsequent inhalation event according to the modification to the timing between the consecutive uses.

2. The method of claim 1, wherein the medication data includes information regarding a type of the respiratory medicament.

3. The method of claim 1, wherein the medication data includes information on a period of time required between consecutive doses of a plurality of medicament types or medicament device types.

4. The method of claim 1, wherein the predetermined modification to the timing between the consecutive uses directs the subsequent inhalation event after more than 30 seconds following the second inhalation event.

5. The method of claim 1, further comprising:
   based on the modification to the timing between the consecutive uses of the respiratory medicament device, classifying the consecutive uses as the proper usage technique or an improper usage technique to generate a usage technique record; and
   based on the usage technique record, providing at least one notification of the proper usage technique or the improper usage technique to ensure the proper usage technique.

6. The method of claim 5, wherein the plurality of consecutive uses is at least two consecutive uses of the respiratory medicament device, the at least two uses being separated in time by less than or equal to 120 seconds.

7. The method of claim 5, wherein:
   the proper usage technique comprises a time period of more than 30 seconds between consecutive uses of the respiratory medicament device; and
   the improper usage technique comprises a time period of less than or equal to 30 seconds between consecutive uses of the respiratory medicament device.

8. The method of claim 5, wherein the at least one notification comprises an identification of the improper usage technique with the guidance on an appropriate usage technique for the respiratory medicament device, the guidance comprising:
   a timer configured to indicate a period of time required between consecutive uses of the respiratory medicament device; and
   an audio or a visual content displaying a required sequence of steps for ensuring the proper usage technique of the respiratory medicament device.

9. A system, comprising:
one or more processors; and
a memory storing instructions that, when executed by the one or more processors, cause the system to perform operations including:
   collecting, by at least one processor associated with a respiratory medicament device, medication data relating to a medication plan for a patient, the medication data including at least one of a type of the respiratory medicament device and a prescribed number of doses of a respiratory medicament associated with the respiratory medicament device;
   based on the medication data, determining whether the respiratory medicament device requires a plurality of consecutive uses;
   based on determining the respiratory medicament device requires a plurality of consecutive uses, determining a timing between consecutive uses of the respiratory medicament device;
   based on determining a spacer is used with the respiratory medicament device, determining a modification to the timing between the consecutive uses;
   detecting, by a medicament sensor associated with the respiratory medicament device, a first set of use data of the respiratory medicament device, the first set of use data including at least a first inhalation event associated with the patient;
   identifying, from the first set of use data, a usage characteristic associated with the patient, the usage characteristic including an audio signal associated with an inhalation of the patient;
   applying an adjustment to the medicament sensor in response to identifying the usage characteristic, the adjustment causing the medicament sensor to eliminate false positives in response to detecting a second set of use data, the second set of use data including at least a second inhalation event associated with the patient;
   detecting, by the medicament sensor, the second set of use data;
   identifying, from the second set of use data, the second inhalation event; and
   based on identifying the second inhalation event, providing a guidance by way of an instruction component to direct a subsequent inhalation event according to the modification to the timing between the consecutive uses.

10. The system of claim 9, wherein the medication data includes information regarding a type of the respiratory medicament.

11. The system of claim 9, wherein the medication data includes information on a period of time required between consecutive doses of a plurality of medicament types or medicament device types.

12. The system of claim 9, wherein the modification to the timing between the consecutive uses directs the subsequent inhalation event after more than 30 seconds following the second inhalation event.

13. The system of claim 9, wherein the operations further include:
   based on the modification to the timing between the consecutive uses of the respiratory medicament device, classifying the consecutive uses as a proper usage technique or an improper usage technique to generate a usage technique record; and
   based on the usage technique record, providing at least one notification of the proper usage technique or the improper usage technique to ensure the proper usage technique.

14. The system of claim 13, wherein the plurality of consecutive uses is at least two consecutive uses of the respiratory medicament device, the at least two uses being separated in time by less than or equal to 120 seconds.

15. The system of claim 13, wherein:
   the proper usage technique comprises a time period of more than 30 seconds between consecutive uses of the respiratory medicament device; and
   the improper usage technique comprises a time period of less than or equal to 30 seconds between consecutive uses of the respiratory medicament device.

16. The system of claim 13, wherein the at least one notification comprises an identification of the improper usage technique with the guidance on an appropriate usage technique for the respiratory medicament device, the guidance comprising:
   a timer configured to indicate a period of time required between consecutive uses of the respiratory medicament device; and
   an audio or a visual content displaying a required sequence of steps for ensuring the proper usage technique of the respiratory medicament device.

17. A non-transitory computer-readable storage medium storing instructions encoded thereon that, when executed by a processor, cause the processor to perform operations comprising:
   collecting, by at least one processor associated with a respiratory medicament device, medication data relating to a medication plan for a patient, the medication data including at least one of a type of the respiratory medicament device and a prescribed number of doses of a respiratory medicament associated with the respiratory medicament device;
   based on the medication data, determining whether the respiratory medicament device requires a plurality of consecutive uses;
   based on determining the respiratory medicament device requires a plurality of consecutive uses, determining a timing between consecutive uses of the respiratory medicament device;
   based on determining a spacer is used with the respiratory medicament device, determining a modification to the timing between the consecutive uses;
   detecting, by a medicament sensor associated with the respiratory medicament device, a first set of use data of the respiratory medicament device, the first set of use data including at least a first inhalation event associated with the patient;
   identifying, from the first set of use data, a usage characteristic associated with the patient, the usage characteristic including an audio signal associated with an inhalation of the patient;
   applying an adjustment to the medicament sensor in response to identifying the usage characteristic, the adjustment causing the medicament sensor to eliminate false positives in response to detecting a second set of use data, the second set of use data including at least a second inhalation event associated with the patient;
   detecting, by the medicament sensor, the second set of use data;
   identifying, from the second set of use data, the second inhalation event; and based on identifying the second inhalation event, providing a guidance by way of an instruction component to direct a subsequent inhalation event according to the modification to the timing between the consecutive uses.

18. The non-transitory computer-readable storage medium of claim 17, wherein the operations further include:
- based on the modification to the timing between the consecutive uses of the respiratory medicament device, classifying the consecutive uses as a proper usage technique or an improper usage technique to generate a usage technique record, wherein the proper usage technique comprises a time period of more than 30 seconds between consecutive uses of the respiratory medicament device, and wherein the improper usage technique comprises a time period of less than or equal to 30 seconds between consecutive uses of the respiratory medicament device; and
- based on the usage technique record, providing at least one notification of the proper usage technique or the improper usage technique to ensure the proper usage technique.

19. The non-transitory computer-readable storage medium of claim 18, wherein the plurality of consecutive uses is at least two consecutive uses of the respiratory medicament device, the at least two uses being separated in time by less than or equal to 120 seconds.

20. The non-transitory computer-readable storage medium of claim 18, wherein the at least one notification comprises an identification of the improper usage technique with the guidance on an appropriate usage technique for the respiratory medicament device, the guidance comprising:
- a timer configured to indicate a period of time required between consecutive uses of the respiratory medicament device; and
- an audio or a visual content displaying a required sequence of steps for ensuring the proper usage technique of the respiratory medicament device.

* * * * *